(12) United States Patent
Haap et al.

(10) Patent No.: US 6,624,182 B1
(45) Date of Patent: Sep. 23, 2003

(54) HYDROXYPHENYLVINYLTHIAZOLES

(75) Inventors: Wolfgang Haap, Grenzach-Wyhlen (DE); Werner Hölzl, Eschentzwiller (FR); Dietmar Ochs, Schopfheim (DE); Karin Puchtler, Fischingen (DE); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 79 days.

(21) Appl. No.: 09/714,716

(22) Filed: Nov. 16, 2000

(30) Foreign Application Priority Data

Nov. 25, 1999 (EP) .............................. 99811090

(51) Int. Cl.$^7$ ............................................. A61K 31/425
(52) U.S. Cl. ..................... 514/365; 514/369; 422/28; 422/37
(58) Field of Search .................... 514/365, 369; 548/146; 422/28, 37

(56) References Cited

U.S. PATENT DOCUMENTS 4,902,700 A    2/1990    Hayasi et al.

FOREIGN PATENT DOCUMENTS

WO          94/08982         4/1994

Primary Examiner—Bennett Celsa
Assistant Examiner—Jon Epperson
(74) Attorney, Agent, or Firm—Kevin T. Mansfield

(57) ABSTRACT

The use of hydroxyphenylvinylthiazoles of formula

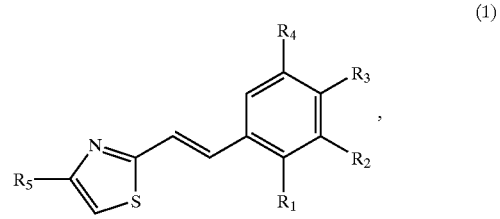

(1)

wherein $R_1$, $R_2$, $R_3$ and $R_4$ are each independently of the others hydrogen; halogen; hydroxy, $C_1$–$C_{16}$-alkyl, $C_1$–$C_{16}$alkoxy, phenyl; phenyl-$C_1$–$C_3$alkyl; $C_6$–$C_{10}$aryloxy, amino, mono-$C_1$–$C_5$alkyl-amino, di-$C_1$–$C_5$alkylamino or -$NO_2$; wherein at least one of the radicals $R_1$, $R_2$, $R_3$ and $R_4$ is hydroxy;

$R_5$ is $C_1$–$C_5$alkyl; $C_1$–$C_5$alkoxy; or unsubstituted or halo-, $C_1$–$C_5$alkyl-, $C_1$–$C_5$alkoxy-, hydroxy- or pyrrolidinyl-substituted phenyl; as microbicidal active ingredients is described. The compounds exhibit a pronounced action against pathogenic gram-positive and gram-negative bacteria, and also against yeasts and moulds. Accordingly, they are suitable for the antimicrobial treatment, especially the preservation and disinfection, of surfaces.

11 Claims, No Drawings

HYDROXYPHENYLVINYLTHIAZOLES

The present invention relates to the use of hydroxyphenylvinylthiazoles in the antimicrobial treatment of surfaces, as an antimicrobial active ingredient against gram-positive and gram-negative bacteria, yeasts and fungi, as well as in the preservation of cosmetics, household products, textiles, plastics and disinfectants.

The hydroxyphenylvinylthiazoles used according to the invention have the formula

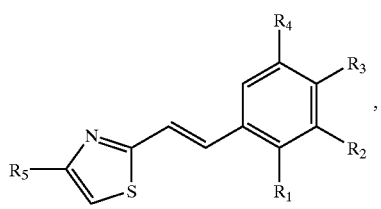
(1)

$R_1$, $R_2$, $R_3$ and $R_4$ are each independently of the others hydrogen; halogen; hydroxy, $C_1$–$C_{16}$-alkyl, $C_1$–$C_{16}$alkoxy, phenyl; phenyl-$C_1$–$C_3$alkyl; $C_6$–$C_{10}$aryloxy, amino, mono-$C_1$–$C_5$alkyl-amino, di-$C_1$–$C_5$alkylamino or -$NO_2$; wherein at least one of the radicals $R_1$, $R_2$, $R_3$ and $R_4$ is hydroxy;

$R_5$ is $C_1$–$C_5$alkyl; $C_1$–$C_5$alkoxy; or unsubstituted or halo-, $C_1$–$C_5$alkyl-, $C_1$–$C_5$alkoxy-, hydroxy- or pyrrolidinyl-substituted phenyl.

$C_1$–$C_{16}$Alkyl radicals are straight-chain or branched alkyl radicals, for example methyl, ethyl, n-propyl, isopropyl, n-butyl, sec-butyl, tert-butyl, pentyl, hexyl, heptyl, octyl, nonyl, decyl, un-decyl, dodecyl, tetradecyl, pentadecyl or hexadecyl.

$C_1$–$C_{16}$Alkoxy is, for example, methoxy, ethoxy, n-propoxy, isopropoxy, n-butoxy, sec-butoxy, tert-butoxy or pentyloxy, hexyloxy, heptyloxy, octyloxy, nonyloxy, decyloxy, undecyloxy, do decyloxy, tetradecyloxy, pentadecyloxy or hexadecyloxy.

Halogen is fluorine, chlorine, bromine or iodine.

The hydroxyphenylvinylthiazoles used according to the invention may be in the form of E or Z isomers. They are preferably in the form of E isomers.

Compounds that are of interest are hydroxyphenylvinylthiazoles of formula (1) wherein $R_1$, $R_2$, $R_3$ and $R_4$ are each independently of the others hydrogen, hydroxy, $C_1$–$C_5$alkyl, $C_1$–$C_5$-alkoxy or phenyl-$C_1$–$C_3$alkyl.

Also of interest are compounds of formula (1) wherein $R_5$ is $C_1$–$C_5$alkyl; or unsubstituted or halo- or pyrrolidinyl-substituted phenyl.

Compounds that are of very special interest have the formula

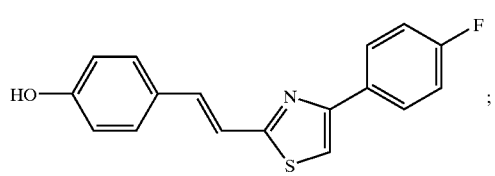
(2)

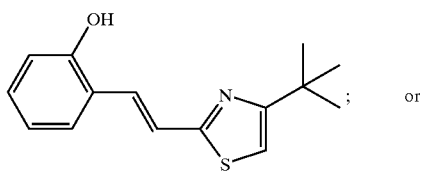
(3)

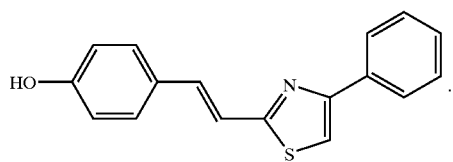
(4)

Further hydroxyphenylvinylthiazoles according to the invention are listed by way of example in Table 1 below:

TABLE 1

General formula:

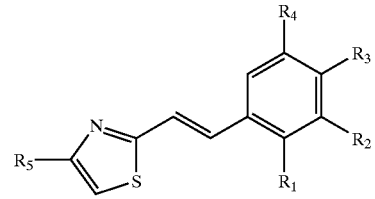

| Compound of formula | $R_1$ | $R_2$ | $R_3$ | $R_4$ | $R_5$ |
|---|---|---|---|---|---|
| (5) | H | OH | H | H | 4-F—Ph |
| (6) | H | OH | OMe | H | 4-F—Ph |
| (7) | H | OEt | OH | H | 4-F—Ph |
| (8) | H | OMe | OH | H | 4-F—Ph |
| (9) | OH | H | OMe | H | 4-F—Ph |
| (10) | OH | H | H | H | 4-F—Ph |
| (11) | H | OH | OMe | OMe | 4-F—Ph |
| (12) | H | Me | OH | Me | 4-F—Ph |
| (13) | OH | Me | H | H | 4-F—Ph |
| (14) | OH | H | OBzl | H | 4-F—Ph |
| (15) | OMe | H | OH | H | 4-F—Ph |
| (16) | H | H | OH | H | t. but |
| (17) | H | OH | H | H | t. but |
| (18) | H | OH | OMe | H | t. but |
| (19) | H | OEt | OH | H | t. but |
| (20) | H | OMe | OH | H | t. but |
| (21) | OH | H | OMe | H | t. but |
| (22) | H | OH | OMe | OMe | t. but |
| (23) | H | Me | OH | Me | t. but |
| (24) | OH | Me | H | H | t. but |
| (25) | OH | H | OBzl | H | t. but |
| (26) | OMe | H | OH | H | t. but |
| (27) | H | H | OH | H | 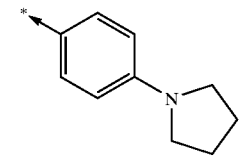 |
| (28) | H | OH | H | H | 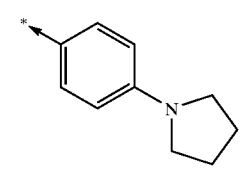 |

TABLE 1-continued

General formula:

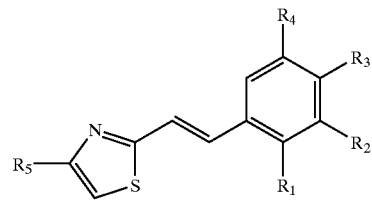

| Compound of formula | R₁ | R₂ | R₃ | R₄ | R₅ |
|---|---|---|---|---|---|
| (29) | H | OH | OMe | H | 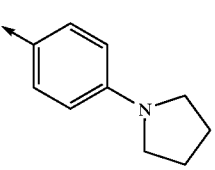 |
| (30) | H | OEt | OH | H | 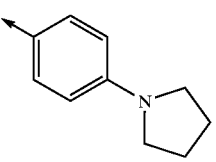 |
| (31) | H | OMe | OH | H | 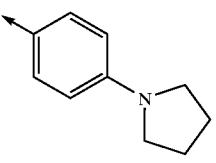 |
| (32) | OH | H | OMe | H | 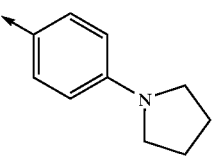 |
| (33) | OH | H | H | H | 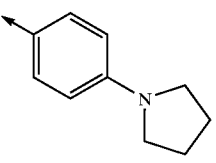 |
| (34) | H | OH | OMe | OMe | 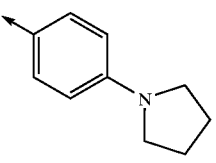 |
| (35) | H | Me | OH | Me | 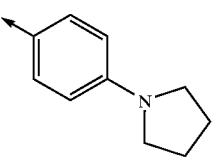 |
| (36) | OH | Me | H | H |  |
| (37) | OH | H | OBzl | H |  |
| (38) | OMe | H | OH | H |  |
| (39) | H | H | OH | H | Et |
| (40) | H | OH | H | H | Et |
| (41) | H | OH | OMe | H | Et |
| (42) | H | OEt | OH | H | Et |
| (43) | H | OMe | OH | H | Et |
| (44) | OH | H | OMe | H | Et |
| (45) | OH | H | H | H | Et |
| (46) | H | OH | OMe | OMe | Et |
| (47) | H | Me | OH | Me | Et |
| (48) | OH | Me | H | H | Et |
| (49) | OH | H | OBzl | H | Et |
| (50) | OMe | H | OH | H | Et |
| (51) | H | OH | H | H | Ph |
| (52) | H | OH | OMe | H | Ph |
| (53) | H | OEt | OH | H | Ph |
| (54) | H | OMe | OH | H | Ph |
| (55) | OH | H | OMe | H | Ph |
| (56) | OH | H | H | H | Ph |
| (57) | H | OH | OMe | OMe | Ph |
| (58) | H | Me | OH | Me | Ph |
| (59) | OH | Me | H | H | Ph |
| (60) | OH | H | OBzl | H | Ph |
| (61) | OMe | H | OH | H | Ph |

The preparation of the hydroxyphenylvinylthiazoles used according to the invention is pre-ferably carried out in a solid-phase synthesis using a trityl resin. The preparation is carried out according to the following scheme:

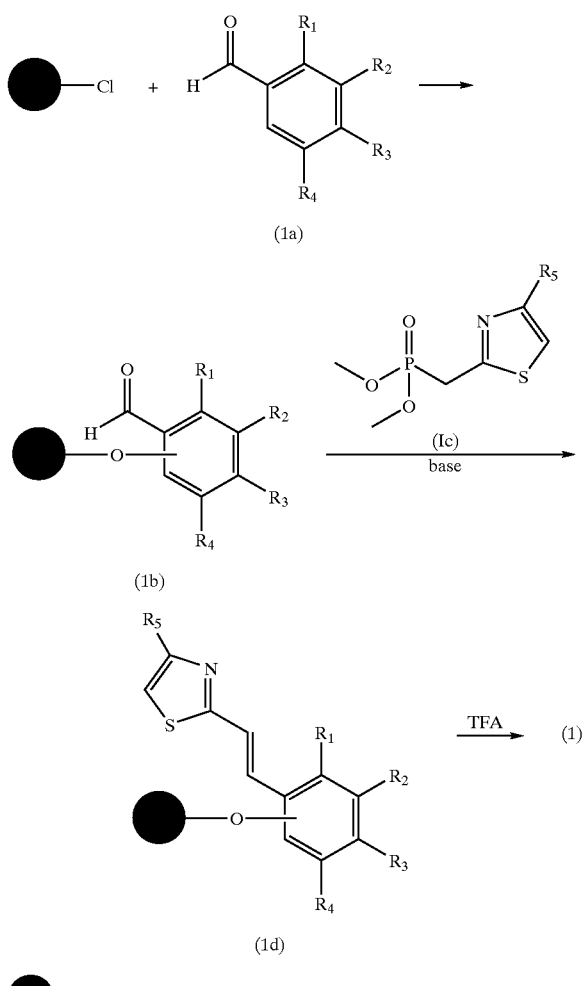

(1a)

(1b)

(1c)

(1d)

● = trityl resin radical

In the above scheme, $R_1$, $R_2$, $R_3$, $R_4$ and $R_5$ are as defined for formula (1).

The method of synthesis is based on that specified in the literature by $R_1$ Willard et al., Chemistry & Biology, 2, 1995, 45–51. The preparation process according to the invention differs in that a trityl resin is used and the method of loading the resin is different.

Further details regarding the preparation process according to the invention will be found in the corresponding Examples.

The thiazol-2-ylmethylphosphonates (compound of formula (1c)) used as starting materials in the preparation according to the invention are prepared according to the known Hantzsch thiazole synthesis:

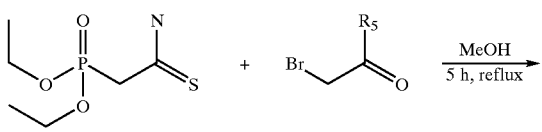

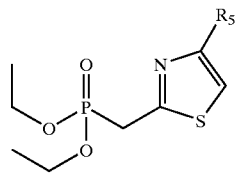

Diethyl (2-amino-2-thioxoethyl)phosphonate (2.1 g; 10 mmol) and bromomethyl ketone (10.5 mmol) are dissolved in methanol (10 ml) under a protective gas atmosphere. The reaction mixture is subsequently heated for 5 hours under reflux and then concentrated to dryness. The residue is taken up in dichloromethane (100 ml) and washed with saturated aqueous $NaHCO_3$ solution (2×50 ml) and NaCl solution (50 ml). The washing solutions are extracted with dichloromethane (25 ml) and the combined organic extracts are concentrated to dry-ness.

Yields: $R_2$=4-F-Ph (87.1%); $R_2$=t. but (84.7%); $R_2$=4-(pyrrolidin-1-yl)-phenyl (98%); $R_2$=Et (86.2%); $R_2$=Ph (100%).

All the compounds are characterised by $^1$H-NMR and show the corresponding chemical shifts.

The hydroxyphenylvinylthiazoles used according to the invention exhibit a pronounced anti-microbial action, especially against pathogenic gram-positive and gram-negative bacteria and also against bacteria of skin flora and, additionally, against yeasts and moulds. Accordingly, they are especially suitable in the disinfection, deodorisation and also the general and antimicrobial treatment of the skin and mucosa and of integumentary appendages (hair), more especially in the disinfection of the hands and of wounds.

Accordingly, they are suitable as antimicrobial active ingredients and preservatives in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, for example cleansing solutions for the skin, moist cleansing cloths, oils or powders.

Accordingly, the invention relates also to a personal care preparation comprising at least one compound of formula (1), and cosmetically tolerable carriers or adjuvants.

The personal care preparation according to the invention comprises from 0.01 to 15% by weight, preferably from 0.1 to 10% by weight, based on the total weight of the composition, of a hydroxyphenylvinylthiazole compound of formula (1), and cosmetically tolerable adjuvants.

Depending on the form of the personal care preparation, it comprises further components in addition to the hydroxyphenylvinylthiazole compound of formula (1), for example sequestering agents, colourants, perfume oils, thickeners or strengthening agents (consistency regulators), emollients, UV absorbers, skin-protecting agents, antioxidants, additives that improve the mechanical properties, such as dicarboxylic acids and/or Al, Zn, Ca, Mg salts of $C_{14}$–$C_{22}$ fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, as a solid stick or as an aerosol formulation.

In the case of a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in a variety of fields. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose and pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and anti-perspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight compound of formula (1)

0.3 to 1% by weight titanium dioxide 1 to 10% by weight stearic acid and ad 100% soap base, e.g. the sodium salts of tallow fatty acid and coconut fatty acid or glycerol.

A shampoo has, for example, the following composition:

0.01 to 5% by weight compound of formula (1)

12.0% by weight sodium laureth-2-sulfate 4.0% by weight cocamidopropyl betaine 3.0% by weight NaCl and water ad 100%.

A deodorant has, for example, the following composition:

0.01 to 5% by weight compound of formula (1)

60% by weight ethanol 0.3% by weight perfume oil and water ad 100%.

The invention relates also to an oral composition, comprising 0.01 to 15% by weight, based on the total weight of the composition, of the compound of formula (1), and orally tolerable adjuvants.

Example of an oral composition:

10% by weight sorbitol

10% by weight glycerol

15% by weight ethanol

15% by weight propylene glycol 0.5% by weight sodium lauryl sulfate 0.25% by weight sodium methylcocyltaurate 0.25% by weight polyoxypropylene/polyoxyethylene block copolymer 0.10% by weight peppermint flavouring 0.1 to 0.5% by weight compound of formula (1) and 48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The hydroxyphenylvinylthiazoles of formula (1) used according to the invention are suitable also in the treatment, especially the preservation, of textile fibre materials. Such materials are natural and dyed or printed fibre materials, for example, of silk, wool, polyamide or poly-urethanes, and especially all kinds of cellulosic fibre materials. Such fibre materials are, for example, natural cellulosic fibres, such as cotton, linen, jute and hemp, and also cellulose and regenerated cellulose. Textile fibre materials of cotton are preferred.

The hydroxyphenylvinylthiazoles according to the invention are suitable also in the treatment, especially the antimicrobial dressing or preservation, of plastics, for example polyethylene, polypropylene, polyurethane, polyester, polyamide, polycarbonate, latex, etc. Fields of use are, for example, floor coverings, plastics coatings, plastics containers and packaging materials; kitchen and bathroom utensils (e.g. brushes, shower curtains; sponges, bathroom mats), latex, filtering materials (air and water filters), plastics articles that are used in the medical field, e.g. dressing materials, syringes, catheters, etc., so-called medical devices, gloves and mattresses.

Paper, for example toilet paper, may also be provided with an antimicrobial dressing using the hydroxyphenylvinylthiazoles according to the invention.

Nonwovens, for example nappies, sanitary towels, panty liners, cloths for the hygiene and household sector, may also be provided with an antimicrobial dressing according to the invention.

The hydroxyphenylvinylthiazoles of formula (1) are also used in washing and cleaning formulations, e.g. in liquid washing agents and washing powders or softeners.

The hydroxyphenylvinylthiazoles may be used especially also in household and multipurpose cleaners for the cleaning and disinfection of hard surfaces.

A cleaning preparation has, for example, the following composition:

| | |
|---|---|
| 0.01 to 5% | compound of formula (1) |
| 3.0% | octyl alcohol 4EO |
| 1.3% | fatty alcohol $C_8$–$C_{10}$polyglucoside |
| 3.0% | isopropanol and |
| ad 100% | water. |

In addition to the preservation of cosmetic and household products, the preservation and antimicrobial dressing of industrial products and use as a biocide in industrial processes is also possible, for example in the treatment of paper, especially in liquors for the treatment of paper, printing thickeners consisting of starch or cellulose derivatives, surface coatings and paints.

The hydroxyphenylvinylthiazole compounds of formula (1) are suitable also for the antimicrobial treatment of wood and for the antimicrobial treatment, preservation and dressing of leather.

The compounds according to the invention are also suitable for protecting cosmetic products and household products against deterioration caused by microbes.

The hydroxyphenylvinylthiazole compounds that can be used according to the invention are known compounds or, alternatively, novel compounds.

The novel compounds have the formula

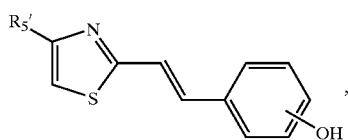

(1')

$R_5'$ is $C_1$–$C_5$alkyl; or halo-substituted phenyl; especially tert-butyl or p-fluorophenyl.

The invention relates also to the compounds of formula (1').

The following Examples serve to illustrate the invention but do not limit the invention.

General Procedure for the Synthesis of the Novel Compounds a) Trityl chloride resin (100 mg, 0.1 mmol) is swelled in dichloromethane (2 ml), and there are added thereto one of the hydroxybenzaldehydes listed below (10 eq., 1 mmol), DIPEA (10 eq., 1 mmol) and a catalytic amount of DMAP. The mixture is shaken for 3 hours at 25° C. The resin is then filtered off with suction and washed intensively with DMF, methanol, dichloromethane and methanol, and dried in vacuo.

IR: 1690 cm$^{-1}$ (C=O valence vibration of the aldehyde)

b) The loaded resin (100 mg, 0.1 mmol) is subsequently suspended in DMF (abs., 3 ml), and there are added thereto one of the 2-thiazolylmethylphosphonates listed below (10 eq., 1 mmol) and also sodium ethanolate or sodium methanolate (10 eq., 1 mmol). The mixture is shaken for 18 hours at 25° C. The resin is then filtered off with suction and washed intensively as indicated above and dried.

IR: C=O valence vibration has disappeared completely c) In order to isolate the resin, 5% TFA in dichloromethane (3 ml) is added thereto, and shaking is carried out for 3 hours at 25° C. The separation solution is filtered off and concentrated to dryness. The residue is lyophilised from tert-butyl alcohol/water (4:1).

All the compounds are analysed by LC-MS and show the expected masses. The purities of the compounds are from 40 to 98% (peak areas in the chromatogram; UV detection at 254 nm).

Some of the compounds are characterised in greater detail by $^1$H-NMR. According to that analysis, the compounds are mainly in the E configuration.

Example: Compound of Formula (2):

LC-MS: Zisomer [M+H]$^+$298; 1.7%; E isomer [M+H]$^+$ 298; 96.9%; Detection at 254 nm; $^1$H-NMR DMSO-D6 [ppm; Hz]: 9.95 (s, broad, OH); 8.10 (dd 8.58 Hz, coupling with F), 8.07 (s, thiazole proton), 7.62 (d, 8.58 Hz), 7.51 (d, 15.8 Hz vinyl proton), 7.38 (d, 15.8 Hz vinyl proton), 7.36 (d, 8.58 Hz), 6.87 (d, 8.58 Hz).

Structural Units Used:

Hydroxybenzaldehydes OHC—$R_1$:

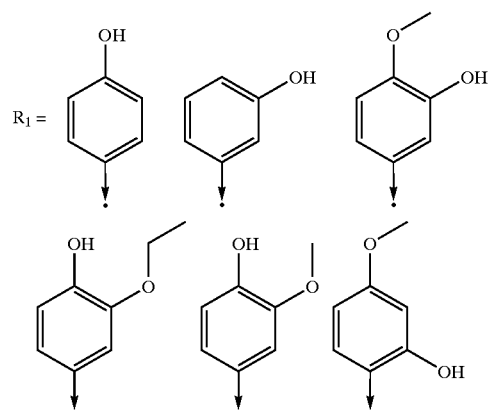

-continued

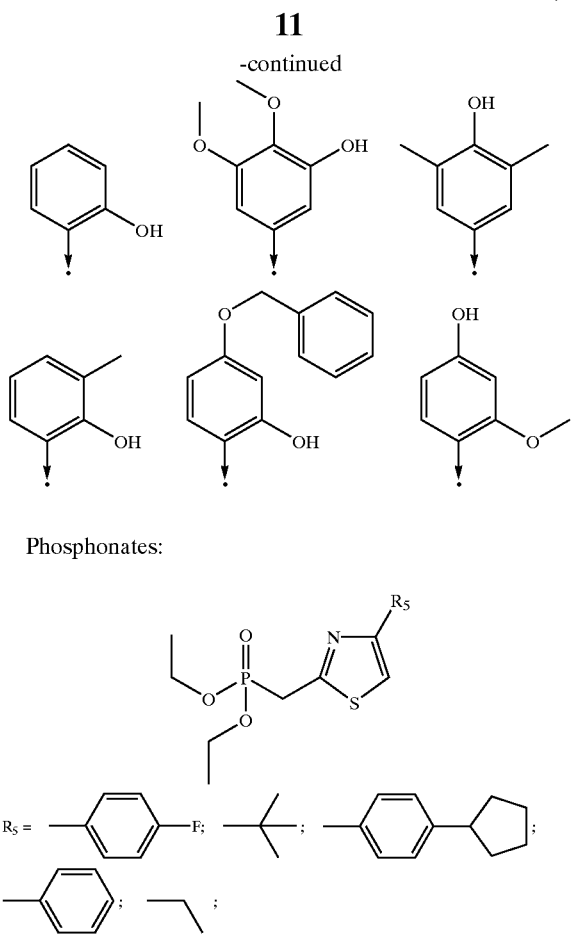

Phosphonates:

With this method, a matrix of 12×5=60 hydroxyphenylvinylthiazoles is obtained. The compounds are listed in Table 1.

The microbiological data determined are summarised in Table 2.

TABLE 2

| | MIC values in ppm for various microorganisms*) | | | | |
|---|---|---|---|---|---|
| Compd. of formula | S. aureus | E. coli | P. aeruginosa | C. albicans | A. niger |
| (2) | >100 | >100 | >100 | 30 | >100 |
| (3) | 60 | >100 | >100 | >100 | >100 |
| (4) | >100 | >100 | >100 | 30 | >100 |
| (5) | >100 | >100 | >100 | >100 | >100 |
| (6) | >100 | >100 | >100 | >100 | >100 |
| (7) | >100 | >100 | >100 | >100 | >100 |
| (8) | >100 | >100 | >100 | >100 | >100 |
| (9) | >100 | >100 | >100 | >100 | >100 |
| (10) | >100 | >100 | >100 | >100 | >100 |
| (11) | >100 | >100 | >100 | >100 | >100 |
| (12) | >100 | >100 | >100 | >100 | >100 |
| (13) | >100 | >100 | >100 | >100 | >100 |
| (14) | >100 | >100 | >100 | >100 | >100 |
| (15) | >100 | >100 | >100 | >100 | >100 |
| (16) | >100 | >100 | >100 | >100 | >100 |
| (17) | >100 | >100 | >100 | >100 | >100 |
| (18) | >100 | >100 | >100 | >100 | >100 |
| (19) | >100 | >100 | >100 | >100 | >100 |
| (20) | >100 | >100 | >100 | >100 | >100 |
| (21) | >100 | >100 | >100 | >100 | >100 |
| (22) | >100 | >100 | >100 | >100 | >100 |
| (23) | >100 | >100 | >100 | >100 | >100 |
| (24) | >100 | >100 | >100 | >100 | >100 |
| (25) | >100 | >100 | >100 | >100 | >100 |

TABLE 2-continued

| | MIC values in ppm for various microorganisms*) | | | | |
|---|---|---|---|---|---|
| Compd. of formula | S. aureus | E. coli | P. aeruginosa | C. albicans | A. niger |
| (26) | >100 | >100 | >100 | >100 | >100 |
| (27) | >100 | >100 | >100 | >100 | >100 |
| (28) | >100 | >100 | >100 | >100 | >100 |
| (29) | >100 | >100 | >100 | >100 | >100 |
| (30) | >100 | >100 | >100 | >100 | >100 |
| (31) | >100 | >100 | >100 | >100 | >100 |
| (32) | >100 | >100 | >100 | >100 | >100 |
| (33) | >100 | >100 | >100 | >100 | >100 |
| (34) | >100 | >100 | >100 | >100 | >100 |
| (35) | >100 | >100 | >100 | >100 | >100 |
| (36) | >100 | >100 | >100 | >100 | >100 |
| (37) | >100 | >100 | >100 | >100 | >100 |
| (38) | >100 | >100 | >100 | >100 | >100 |
| (39) | >100 | >100 | >100 | >100 | >100 |
| (40) | >100 | >100 | >100 | >100 | >100 |
| (41) | >100 | >100 | >100 | >100 | >100 |
| (42) | >100 | >100 | >100 | >100 | >100 |
| (43) | >100 | >100 | >100 | >100 | >100 |
| (44) | >100 | >100 | >100 | >100 | >100 |
| (45) | >100 | >100 | >100 | >100 | >100 |
| (46) | >100 | >100 | >100 | >100 | >100 |
| (47) | >100 | >100 | >100 | >100 | >100 |
| (48) | >100 | >100 | >100 | >100 | >100 |
| (49) | >100 | >100 | >100 | >100 | >100 |
| (50) | >100 | >100 | >100 | >100 | >100 |
| (51) | >100 | >100 | >100 | >100 | >100 |
| (52) | >100 | >100 | >100 | >100 | >100 |
| (53) | >100 | >100 | >100 | >100 | >100 |
| (54) | >100 | >100 | >100 | >100 | >100 |
| (55) | >100 | >100 | >100 | >100 | >100 |
| (56) | >100 | >100 | >100 | >100 | >100 |
| (57) | >100 | >100 | >100 | >100 | >100 |
| (58) | >100 | >100 | >100 | >100 | >100 |
| (59) | >100 | >100 | >100 | >100 | >100 |
| (60) | >100 | >100 | >100 | >100 | >100 |
| (61) | >100 | >100 | >100 | >100 | >100 |

*)The MIC values were determined by measuring the optical density at concentrations of the substances between 100; 10 and 1 ppm. In that respect, some of the data are approximate values of the activity. The MIC values of the compounds having good activity (compounds of formulae (2), (3) and (4)) were determined by measuring the optical density at concentrations between 120; 60; 30; 15; 7.5; 3.75 ppm.

Determination of the Minimum Inhibitory Concentration (MIC Value) in Microtitre Plates Nutrient Medium Casein/soybean flour/peptone bouillon for the preparation of preliminary cultures of the test bacteria and yeast.

Mycological slant agar for the preliminary culture of moulds

Examples of Test Microbes:
  Bacteria:
    *Staphylococcus hominis* DMS 20328
    *Escherichia coli* NCTC 8196
    *Pseudomonas aeruginosa* CIP A-22
  Yeast:
    *Candida albicans* ATCC 10231
  Mould:
    *Aspergillus niger* ATCC 6275

Procedure:
The test substances are pre-dissolved in dimethyl sulfoxide (DMSO) and tested in a series of dilutions of 1:2.

Bacteria and yeast are cultured overnight in CASO bouillon; the mould is cultured on myco-logical slant agar and sponged off with 10 ml of 0.85% sodium chloride solution (+0.1% Triton X-100).

All the test microbes are adjusted to a germ count of 1–5×10⁶ KBE/ml using 0.85% sodium chloride solution.

The test substances are pre-pipetted into microtitre plates in an amount of 8 μl per well.

Pre-diluted microbe suspensions are diluted 1:100 in CASO bouillon (bacteria and yeast) or Sabouraud 2% glucose bouillon (mould) and added to the test substances in an amount of 192 μl per well.

The test batches are incubated for 48 hours at 37° C. (bacteria and yeast) or for 5 days at 28° C. (mould).

After incubation, the growth is determined by means of the clouding of the test batches (optical density) at 620 nm in a microplate reader.

The concentration of substance at which (compared with the growth control) a marked inhibition of growth (≦20% growth) of the test microbes can be observed is given as the minimum inhibitory concentration (MIC value).

One microtitre plate is used per test microbe and substance concentration. All substances are tested in duplicate.

What is claimed is:

1. A method for the treatment of surfaces comprising applying to these surfaces an antimicrobially effective amount of a hydroxyphenylvinylthiazole of formula

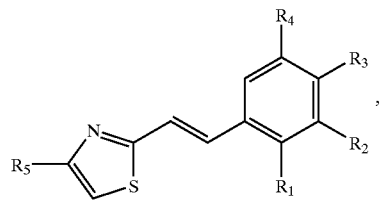

wherein
$R_1$, $R_2$, $R_3$ and $R_4$ are each independently of the others hydrogen, halogen, hydroxy, $C_1$–$C_{16}$alkyl, $C_1$–$C_{16}$alkoxy, phenyl, phenyl-$C_1$–$C_3$alkyl, $C_6$–$C_{10}$aryloxy, amino, mono-$C_1$–$C_5$alkylamino, di-$C_1$–$C_5$alkylamino or -$NO_2$, wherein at least one of the radicals $R_1$, $R_2$, $R_3$ and $R_4$ is hydroxy;
$R_5$ is $C_1$–$C_5$alkyl, $C_1$–$C_5$alkoxy, unsubstituted phenyl, or halo-, $C_1$–$C_5$alkyl-, $C_1$–$C_5$alkoxy-, hydroxy- or pyrrolidinyl-substituted phenyl.

2. A method according to claim 1, wherein
$R_1$, $R_2$, $R_3$ and $R_4$ are each independently of the others hydrogen, hydroxy, $C_1$–$C_5$alkyl, $C_1$–$C_5$-alkoxy or phenyl-$C_1$–$C_3$alkyl.

3. A method according to claim 2, wherein
$R_5$ is $C_1$–$C_5$alkyl, or unsubstituted or halo- or pyrrolidinyl-substituted phenyl.

4. A method according to claim 1, wherein the compound of formula

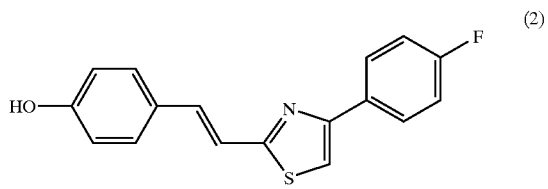

is used.

5. A method according claim 1, wherein the compound of formula

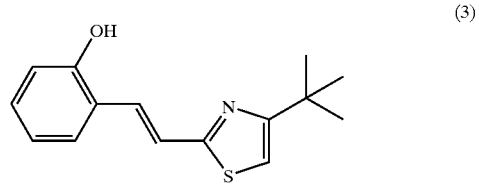

is used.

6. A method according to claim 1, wherein the compound of formula

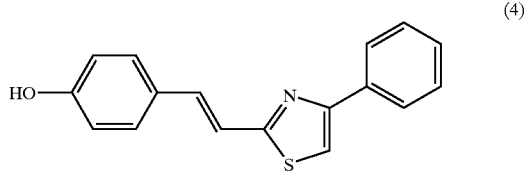

is used.

7. A method according to claim 1, wherein the compound of formula (1) is in the E or Z form.

8. A method according to claim 7, wherein the compound of formula (1) is in the E form.

9. A method for the antimicrobial, treatment, deodorisation and disinfection of the skin, mucosa and hair comprising applying to the skin, mucosa and hair a compound of formula (1) according to claim 1.

10. A method for the treatment of textile fiber materials comprising applying to the fiber materials a compound of formula (1) according to claim 1.

11. A method for the antimicrobial dressing of plastics, paper, nonwovens, wood or leather comprising applying to these materials an antimicrobially effective amount of a compound of formula (1).

* * * * *